United States Patent [19]

Batz et al.

[11] Patent Number: 4,845,030

[45] Date of Patent: Jul. 4, 1989

[54] USE OF ANILINE DERIVATES AS COUPLING COMPONENTS IN OXIDATIVE COLOUR FORMATION REACTIONS

[75] Inventors: Hans-Georg Batz, Tutzing; Rupert Herrmann, Weilheim; Fritz Topfmeier, Heidelberg; Helmut Schlumberger, Polling, all of Fed. Rep. of Germany

[73] Assignee: Boehringer Mannheim GmbH, Mannheim, Fed. Rep. of Germany

[21] Appl. No.: 122,600

[22] Filed: Nov. 20, 1987

Related U.S. Application Data

[63] Continuation of Ser. No. 752,913, Jul. 8, 1985.

[30] Foreign Application Priority Data

Jul. 9, 1984 [DE] Fed. Rep. of Germany ....... 3425219

[51] Int. Cl.$^4$ .............................................. C12Q 1/28
[52] U.S. Cl. ........................................ 435/28; 436/95; 436/135
[58] Field of Search ...................... 438/25, 28; 436/95, 436/128, 131, 135

[56] References Cited

U.S. PATENT DOCUMENTS

| | | |
|---|---|---|
| 3,290,117 | 12/1966 | Adams, Jr. et al. |
| 3,886,045 | 5/1975 | Meiattini .................. 435/28 |
| 3,986,833 | 10/1976 | Mast et al. ................ 436/904 |
| 4,396,714 | 8/1983 | Maeda et al. |
| 4,439,527 | 3/1984 | Pakebusch et al. .......... 436/135 |

FOREIGN PATENT DOCUMENTS

| | | |
|---|---|---|
| 649682 | 12/1964 | Belgium . |
| 0161482 | 10/1985 | European Pat. Off. . |
| 3037342 | 11/1981 | Fed. Rep. of Germany . |
| 53-40585 | 4/1978 | Japan ................... 436/135 |

OTHER PUBLICATIONS

Rose et al.; CA90:43672w–Hair Color Compositions Containing Quinoline & Tetrahydroquinoline.
CA90.43672w–Rose et al. Hair Color Compositions Containing Quinoline and Tetrahydroquinoline.
CRC Handbook of Chem. & Phy. 1969–1970, pp. C-596, C-475, C-477.

*Primary Examiner*—Michael S. Marcus
*Attorney, Agent, or Firm*—Felfe & Lynch

[57] ABSTRACT

The present invention is concerned with the use of aniline derivatives of the general formula:

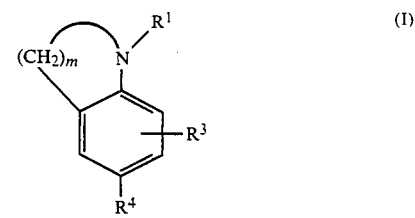

wherein $R^1$ is a hydrogen atom or a $-(CH_2)_n-X$ radical, in which n is a whole number of from 1 to 3, X is H, OH, $NH_2$, $CH_3CONH$, $CH_3SO_2NH$, COOH, $SO_3H$ or $-ArSO_3H$, Ar being an optionally substituted arylene radical, m is a whole number of from 2 to 4, $R^3$ is a hydrogen atom, an alkyl radical containing up to 3 carbon atoms, $OCH_3$, $CH_3CONH$, COOH or $SO_3H$ and $R^4$ is a hydrogen, chlorine or bromine atom or a carboxylic acid or sulphonic acid group, as coupling components in oxidative color formation reactions.

The present invention also provides an agent for the analytical determination of oxidizing substances by oxidative color coupling which, as coupling component, contains at least one compound of general formula (I).

5 Claims, 2 Drawing Sheets

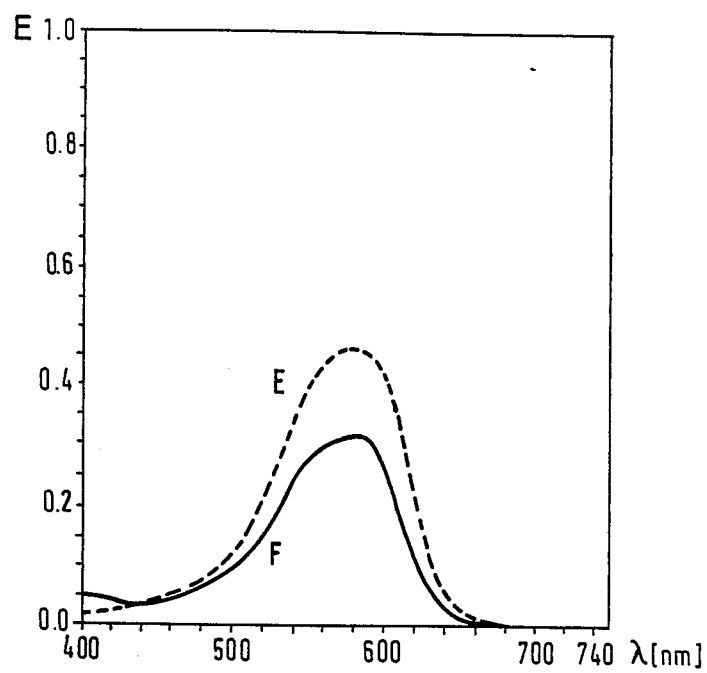

USE OF ANILINE DERIVATES AS COUPLING COMPONENTS IN OXIDATIVE COLOR FORMATION REACTIONS

This application is a continuation of application Ser. No. 752,913, filed July 8, 1985, now abandoned.

BACKGROUND OF THE INVENTION

The present invention is concerned with the use of aniline derivatives as coupling components in oxidative colour formation reactions.

The oxidative colour coupling (Emerson-Trinder reaction) of phenols or anilines with suitable coupling components, for example with 4-aminoantipyrine (4-AAP) or with methylbenzthiazolone hydrazone (MBTH), can serve for the detection and determination of the oxidation agent used for the colour coupling. This reaction can be employed as a basis for chemical diagnostic processes in enzymatic analyses or also in other fields, such as in immunology, for example for the determination of glucose, uric acid or cholesterol in body fluids, by determination of the hydrogen peroxide which is formed in the case of the oxidation of these substances with enzymes, such as glucose oxidase, uricase and cholinesterase, for substrate and/or peroxidase determinations with hydrogen peroxide as oxidation agent and also for the determination of peroxides, for example lipid peroxides, in body fluids (cf., for example Federal Republic of Germany Patent Specification No. 30 37 342).

An important prerequisite for such methods of determination is a high sensitivity, i.e. the formation of coloured materials with a high extinction coefficient and in high yield. This is important, for example, especially in clinical-chemical diagnosis in the case of the determination of substances which only occur in body fluids in small amounts, since disturbance due, for example, to serum components can be substantially excluded. However, in the same way as in the case of clinical-chemical diagnosis, also in other fields, for example in immunology, where peroxidase is often employed as marker enzyme, there is a need for sensitive chromogenic systems.

It is known that in the case of oxidative coupling of phenols with coupling components suitable for colour formation, for example with 4-aminoantipyrine (4-AAP) or methylbenzthiazolone hydrazone (MBTH), the colour yield, referred to the amount of oxidation agent, can be increased when, in the coupling reaction, there are used phenols which are chlorinated or brominated in the 4-position. This effect is due to the fact that the colour formation reaction with halogenated phenols is a 2-electron oxidation process, whereas the phenols which are unsubstituted in the 4-position are converted in a 4-electron oxidation process into the coloured compounds (cf., for example, Japanese Patent Specification No. 9821/79). Thus, the sensitivity in the case of the determination of oxidation agents, for example $Fe^{3+}$ or enzymatically formed hydrogen perioxide, is doubled when 4-halogenophenols are used in the colour formation reaction.

In contradistinction to the halogenophenols aniline derivatives which are substituted by chlorine or bromine in the 4-position show little or no colour formation in the case of oxidative coupling with 4-AAP or MBTH (cf., J. Org. Chem., 3, 153/1938; Analytical Chemistry, 33, 722/1961), whereas the compounds containing hydrogen but otherwise analogous, as a rule give coloured materials with higher extinction coefficients and longer-waved absorption maxima than phenols, especially in the neutral to weakly acidic pH range. N-substituted anilines which are substituted in the o- or p-position by a lower alkyl radical also do not give satisfactory results with regard to sensitivity and colour stability (cf. Federal Republic of Germany Patent Specification No. 28 33 612).

Consequently, attempts have not been lacking to develop new and sensitive chromogenic systems for the determination of oxidation agents, for example hydrogen peroxide and peroxidase (POD). In the case of the oxidative coupling, the developments led to improved anilinic coupling components, the increase in sensitivity thereby mostly being achieved by variation of the substituents on the anilinic nitrogen or on the C3 atom (cf., for example, Federal Republic of Germany Patent Specifications Nos. 30 37 342 and 28 33 612; and European Patent Specification No. 0007787).

SUMMARY OF THE INVENTION

Therefore it is an object of the present invention to make available new aniline derivatives which, in the case of oxidative coupling, lead, with higher yield and sensitivity, to coloured materials with higher extinction and colour stability and which, tehrefore, form a sensitive chromogenic system in the case of oxidative colour coupling.

The subject of the present invention is the use of aniline derivative of the general formula:

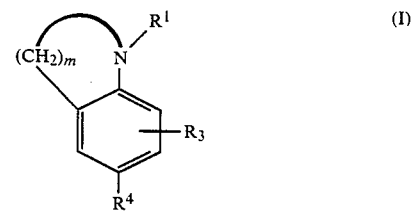

wherein $R^1$ is a hydrogen atom or a $-(CH_2)_n-X$ radical, in which n is a whole number of from 1 to 3 and X is H, OH, $NH_2$, $CH_3CONH$, $CH_3SO_2NH$, COOH, $SO_3H$ or $ArSO_3H$, Ar being an optionally substituted arylene radical, m is a whole number of from 2 to 4 and is preferably 3, $R^3$ is H, an alkyl radical containing up to 3 carbon atoms, $OCH_3$, $CH_3CONH$, COOH or $SO_3H$ and $R^4$ is a hydrogen, chlorine or bromine atom or COOH or $SO_3H$, as coupling components in oxidative colour formation reactions.

The radical Ar can be substituted or preferably unsubstituted and is, for example, a 1,4-naphthylene or especially a 1,4-phenylene radical. A substituted arylene radical can contain one or more and preferably one or two substituents, for example alkyl with up to 3 carbon atoms, OH, $OCH_3$, $SO_3H$ and/or halogen, especially chlorine.

An alkyl radical with up to 3 carbon atoms in the definition of $R^3$ is a methyl, ethyl, n-propyl or isopropyl radical.

Especially preferred are aniline derivatives of the general formula:

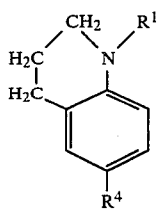

(II)

wherein $R^1$ and $R^4$ have the same meanings as in general formula (I) but in which $R^1$ is preferably a $—(CH_2)_n—X$ radical, n being 2 or 3 and X being OH, $NH_2$, $CH_3CONH$, $CH_3SO_2NH$, COOH or $SO_3H$ and $R^4$ is preferably a hydrogen atom.

We have found that the spectra of the coloured materials formed in the case of the oxidative coupling of the aniline derivatives of general formula (I) with colour couplers surprisingly show higher $\epsilon$-values, as well as very broad extinction maxima, the latter reducing the dependency upon a quite definite wavelength (cf., for example FIGS. 1 to 3 of the accompanying drawings). Furthermore, the aniline derivatives of general formula (I) according to the present invention, in comparison with the corresponding non-cyclic N-alkyl and N,N-dialkyl compounds, surprisingly also show a substantially improved colour stability and a lower blank creep in the case of the oxidative coupling reaction with colour couplers, for example with methylbenzthiazolone hydrazone (MBTH) or with sulphonated methylbenzthiazolone hydrazone (SMBTH), a higher selectivity thereby being obtained.

The compounds of general formula (I) substituted by polar groups also show an improved solubility and, in some cases, especially with alkylsulphonic acid or sulphonic acid groups, a good water-solubility. However, by the use of suitable, conventional detergents, the less soluble compounds of general formula (I) can also be converted into a stable solution.

In the following Table I, there are compared the extinction coefficients ($cm^2/\mu mol\ H_2O_2$) measured at $\lambda_{max}$ of chromogenic systems oxidised with $H_2O_2$/POD, which contain conventional anilinic coupling components and a colour coupler, and the extinction coefficients of otherwise equal chromogenic systems which, however, instead of the conventional anilinic coupling components, contain an appropriately substituted aniline derivative of general formula (I) used according to the present invention. As colour coupler, there was used sulphonated methylbenzthiazolone hydrazone (SMBTH).

The coupling reaction takes place in known manner (cf., for example, Federal Republic of Germany Patent Specification No. 28 33 612); it is preferable to operate at ambient temperature, whereby a concentration ratio of coupling component/colour coupler of >5 has proved to be especially preferred. The pH values are preferably in the neutral range. The following values form the basis for Table I (concentrations in the reaction mixture):

Concentration in the reaction mixture:

| | |
|---|---|
| potassium phosphate buffer, pH 7.0 | 0.1 mol/liter |
| anilinic coupling component | $3 \times 10^{-1}$ mmol/liter |
| colour coupler (SMBTH) | $3 \times 10^{-2}$ mmol/liter |
| hydrogen peroxide | $1.5 \times 10^{-2}$ mmol/liter |
| peroxidase | 1.2 U/ml. |

TABLE I

| coupling component | $\lambda_{max}$(nm) | $\epsilon(cm^2/\mu mol\ H_2O_2)$ |
|---|---|---|
| EMAE[1] | 581 | 20.8 |
| EHT[2] | 573 | 17.0 |
| EST[3] | 584 | 19.2 |
| compound of general formula I: | | |
| $R^1 = —CH_2—CH_2—NH—CO—CH_3$; m = 3 $R^3$ =7-$CH_3$; $R^4$ = H | 557 | 27.2 |
| compounds of general formula II: | | |
| $R^1 = —CH_2—CH_2—NH—CO—CH_3$; $R^4$ = H | 581 | 30.7 |
| $R^1 = —CH_2—CH_2OH$; $R^4$ = H | 571 | 30.5 |
| $R^1 = —(CH_2)_3—SO_3H$; $R^4$ = H | 573 | 31.1 |

[1]N—(2-acetamidoethyl)-N—ethyl-3-methylaniline
[2]N—ethyl-N—(2-hydroxyethyl)-3-methylaniline
[3]N—ethyl-N—(3-methylphenyl)-2-aminoethanesulphonic acid It can be seen from Table I that with the aniline derivatives used according to the present invention, under otherwise the same conditions, there are obtained substantially higher extinction values (by a factor of 1.3 to 1.8); thus, with the compounds according to the present invention, coupling components are made available, the use of which with conventional colour couplers gives a very sensitive chromogenic system for the oxidative colour coupling. The compounds of general formula (I) are especially used for the determination of hydrogen peroxide and of peroxidase.

The present invention also provides an agent for the analytical determination of oxidising substances, especially of hydrogen peroxide, by oxidative coupling, which is characterised in that, as coupling components, it contains a compound according to the present invention of general formula (I) or preferably of general formula (II).

As colour couplers, there can be used those which are conventional for such colour coupling reactions, for example sulphonated methylbenzthiazolone (SMBTH).

The coloured materials obtained in the case of the oxidative colour coupling from the coupling components used according to the present invention and the colour coupler can easily be reduced to the corresponding leuco-coloured materials which can be reoxidised again and, therefore, can also be used for the detection of oxidising substances, for example of hydrogen peroxide in body fluids.

The compounds of general formula (I) are either known or can be prepared according to known synthetic routes, for example by alkylation of aniline derivatives of general formula (I), in which $R^1$ is a hydrogen atom, with compounds of the general formula $Cl—(CH_2)_n—X$, in which X and n have the above-given meanings (cf., for example, Houben-Weyl, Methoden der Organischen Chemie, Vol. 11/1, Cap. II and III; Vol. 2/2, page 251).

The aniline derivative of general formula (I), in which $R^1$ is a hydrogen atom, which are used as starting materials can be obtained, for example, by the catalytic hydrogenation of the corresponding quinoline derivatives (cf., Houben-Weyl, Vol. 4/1c, page 271).

BRIEF DESCRIPTION OF THE DRAWINGS

FIGS. 1 to 3 of the accompanying drawings show the spectra of the chromogenic systems of the coupling components set out in Table I with sulphonated methylbenzthiazolone hydrazone (SMBTH) as colour coupler in the case of the colour formation by oxidation with hydrogen peroxide/peroxidase. The concentrations in the reaction mixture correspond to the values driven in Table I.

DESCRIPTION OF THE PREFERRED EMBODIMENTS

Figure 1:
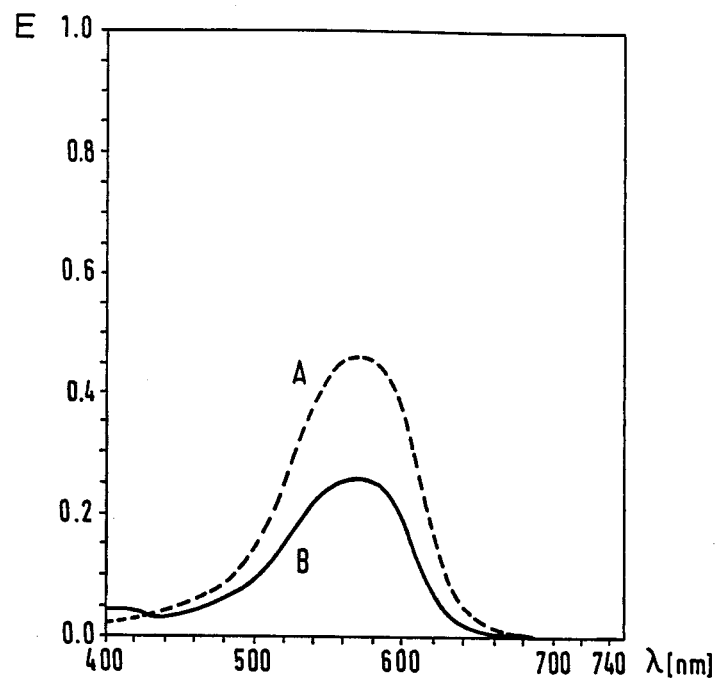
Figure 2:
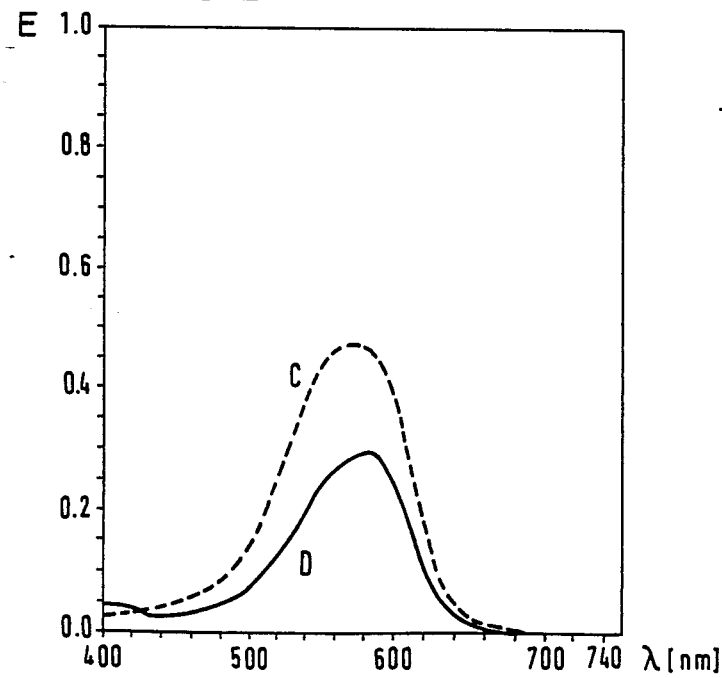

In the Figures, the curves A to F mean the spectra obtained with the following coupling components in which the extinction $\epsilon$ is plotted against the wavelength $\lambda$(nm):
A: formula II, $R^1 = -CH_2CH_2OH$; $R^4 = H$
B: EHT
C: formula II, $R^1 = -CH_2CH_2CH_2SO_3H$; $R^4 = H$
D: EST
E: formula II, $R^1 = -CH_2CH_2NHCOCH_3$; $R^4 = H$
F: EMAE A comparison of the spectra shows that the spectra obtained with the compounds used according to the present invention in comparison with those with similarly substituted conventional anilinic coupling components display, in particular, substantially higher $\epsilon$ values and a broader maximum.

The following Examples describe the preparation of some of the aniline derivatives used according to the present invention:

EXAMPLE 1

N-(2-Hydroxyethyl)-1,2,3,4-tetrahydroquinoline 13.3 g. (0.1 mol) 1,2,3,4-tetrahydroquinoline and 16.1 g. (0.2 mol) 2-chloroethanol were heated for 4 hours to 120° C. After cooling, the reaction mixture was mixed with 200 ml. water and rendered alkaline with 2N aqueous sodium hydroxide solution. Subsequently, the mixture was extracted twice with chloroform and the organic phase was dried over anhydrous sodium sulphate and evaporated on a rotary evaporator. The residue was purified column chromatographically on silica gel (elution with xylene/methyl ethyl ketone=1/1 v/v). Yield: 10.5 g. (59% of theory); mass spectrum: M+ =177.

N-(2-Acetamidopropyl)-1,2,3,4-tetrahydroquinoline was obtained in an analogous way by reacting 1,2,3,4-tetrahydroquinoline with 2-acetamidopropyl chloride.

EXAMPLE 2

1,2,3,4-Tetrahydroquinoline-N-propanesulphonic acid 48.8 molten propane-1,3-sultone were added dropwise at 60+ to 80° C. within the course of 50 minutes to 58.4 g 1,2,3,4-tetrahydroquinoline in a 500 ml. flask. The reaction mixture was left for 3.45 hours at about 70° C. and subsequently 470 ml. methanol were added portionwise under reflux conditions and further stirred under reflux conditions until the solid, glasslike under material had dissolved completely. Thereafter, the reaction mixture was cooled to ambient temperature, while stirring, a rapid crystallization thereby taking place. After leaving to stand for about 12 hours in a refrigerator, the crystals were filtered off. Yield about 50 g.; m.p. 233°–237° C.

EXAMPLE 3

6-Bromo-1,2,3,4-tetrahydroquinoline-N-propanesulphonic acid (a) Bromination of 1,2,3,4-tetrahydroquinoline:

16 g. Bromine, dissolved in 70 ml. glacial acetic acid, were added dropwise within the course of 50 minutes, while stirring intensively, to a solution of 13.3 g. 1,2,3,4-tetrahydroquinoline in 60 ml. glacial acetic acid at a temperature of 10° to 15° C. (cooling with ice water). The crystalline slurry formed was diluted with 3×30 ml. glacial acetic acid, further stirred for 10 to 15 minutes and 200 ml. saturated sodium acetate solution were added thereto, followed by 300 ml. diethyl ether. After diluting with water to 2 litres, the ethereal phase was separated off, washed twice with water, dried with anhydrous sodium sulphate and evaporated in a vacuum at 30° C., 19.3 g. of a brown, oily residue being obtained. The residue was subjected to column chromatography (silica gel: diisopropyl ether/chloroform/glacial acetic acid). From the first substance-containing fractions (fractions 1–8, each of 15 ml.) were obtained 6.23 g. 5,6-dibromo-1,2,3,4-tetrahydroquinoline and from the last fractions (16 - 28, each of 15 ml.) 3.75 g. 6-bromo-1,2,3,4-tetrahydroquinoline; m.p. 30°–34° C.

(b) 6-Bromo-1,2,3,4-tetrahydroquinoline-N-propanesulphonic acid.

4.2 g of the 6-bromo-1,2,3,4-tetra-hydroquinoline obtained according to a) above were dissolved in 0 ml. acetone and, while stirring at 50° C., 2.44 g. molten propane-1,3-sultone, dissolved in 20 ml. acetone, were added dropwise within the course of 30 minutes. After boiling under reflux for 24 hours, a further 2.44 g. molten propanesultone, dissolved in 20 ml. acetone, were added dropwise under the same conditions. After boiling under reflux for 48 hours, the reaction mixture was subjected to column chromatography (silica gel; elution agent chloroform/methanol=1/1 v/v; 25 ml. fractions); fractions 6–10 were evaporated in a vacuum at 35° C., the 1.8 g. of red-brown residue obtained was stirred with about 20 ml. methanol and 1.05 g of sand-coloured crystals were obtained; m.p. 217° C. (decomp.).

5,6-Dibromo-1,2,3,4-tetrahydroquinoline-N-propanesulphonic acid was obtained in an analogous manner from the 5,6-dibromo-1,2,3,4-tetrahydroquinoline obtained according to a) above.

EXAMPLE 4

N-(2-Acetamidoethyl)-1,2,3,4-tetrahydroquinoline 13.3 g. (0.1 mol) 1,2,3,4-tetrahydroquinoline and 9.4 g. (0.11 mol) acetylaziridine were boiled overnight under reflux in 200 ml. anhydrous methanol. After evaporating in a rotary evaporator, the mixture obtained of unreacted starting material and reaction product (13 g.) was purified by column chromatography on silica gel (elution agent: chloroform/acetone=4/1 v/v; m.p. 102° C.

EXAMPLE 5

N-(2-Acetamidoethyl)-7-methyl-1,2,3,4-tetrahydroquinoline 4 g. (27 mmol) 7-methyl-1,2,3,4-tetrahydroquinoline and 2.5 g. (30 mmol) N-acetylaziridine in 100 ml. anhydrous ethanol were boiled under reflux for 1 hour and the reaction mixture was subsequently evaporated in a vacuum. The reaction product was purified by column chromatography on silica gel (elution agent: chloroform/acetone - 4/1 v/v) and recrystallisation from diisopropyl ether. Yield: 1.3 g.; m.p. 99° C.

I claim:

1. In a method for measuring peroxidase or hydrogen peroxide in the presence of peroxidase using a chromogenic system with a coupling component and a color coupler, the amount of colored material formed being measured as a measure of the peroxidase or the hydrogen peroxide to be determined, the improvement comprising using, as the coupling component, an anilie derivative of the formula

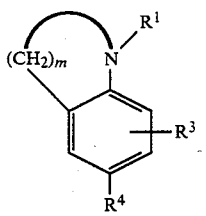

wherein $R^1$ is hydrogen or $-(CH_2)_n-X$, in which n is a whole number of from 1 to 3, X is H, OH, $NH_2$, $CH_3CONH$, $CH_3SO_2NH$, COOH, $SO_3H$ or $-Ar-SO_3H$, Ar being arylene or arylene substituted one or two times with $C_1-C_3$ alkyl, OH, $OCH_3$, $SO_3H$ or halogen, m is a whole number of from 2 to 4, $R^3$ is hydrogen, alkyl containing up to 3 carbon atoms, $OCH_3$, $CH_3CONH$, COOH or $SO_3H$ and $R^4$ is hydrogen, chlorine or bromine or a carboxylic acid or sulphonic acid group.

2. The method of claim 1 wherein the aniline derivative has the formula

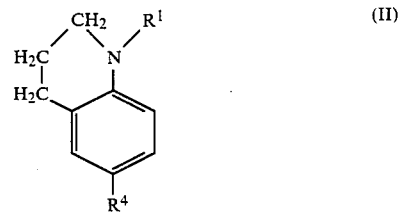

wherein $R^1$ is $-(CH_2)_n-X$, n is 2 or 3, X is OH, $NH_2$, $CH_3CONH$, $CH_3SO_2NH$, COOH or $SO_3H$ and $R^4$ is hydrogen, chlorine or bromine or a carboxylic acid or sulphonic acid group.

3. The method of claim 7 wherein $R^4$ is hydrogen.

4. The method of claim 1 wherein the color coupler is methylbenzthiazolone hydrozoline (MBTH) or sulphonated methylbenzthiazolone hydrazone (SMBTH).

5. The method of claim 1 wherein the color coupler is methylbenzthiazolone hydrazone (MBTH) or sulphonated methylbenzthiazoline hydrazone (SMBTH).

* * * * *

UNITED STATES PATENT AND TRADEMARK OFFICE
CERTIFICATE OF CORRECTION

PATENT NO.  : 4,845,030
DATED       : July 4, 1989
INVENTOR(S) : Hans-Georg Batz, et al.

It is certified that error appears in the above-identified patent and that said Letters Patent is hereby corrected as shown below:

Col. 2, line 29:     change "tehrefore" to -- therefore --.

Col. 5, line 61:     change "60+" to -- 60 --.

Col. 6, line 36:     change "0 ml." to -- 20 ml. --.

Col. 7, line 20      change "anilie" to --aniline--.

Col. 8, line 26      change "claim 7" to -- claim 1 --.

Signed and Sealed this

Twenty-fourth Day of July, 1990

Attest:

HARRY F. MANBECK, JR.

*Attesting Officer*  *Commissioner of Patents and Trademarks*